US00PP16524P2

(12) United States Plant Patent
Trees

(10) Patent No.: US PP16,524 P2
(45) Date of Patent: May 9, 2006

(54) ***LOBELIA* PLANT NAMED 'BALOBWABLU'**

(50) Latin Name: *Lobelia erinus*
Varietal Denomination: Balobwablu

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 61 days.

(21) Appl. No.: 11/016,491

(22) Filed: Dec. 17, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Lobelia* plant named 'Balobwablu' characterized by its mounded and trailing growth habit, dark lavender blue-colored flowers, dark-green colored foliage, and day length neutral flowering habit.

1 Drawing Sheet

Latin name of genus and species of plant claimed: *Lobelia erinus*.
Variety denomination: 'Balobwablu'.

BACKGROUND OF THE INVENTION

The present invention relates to a new and distinct *Lobelia* plant hereinafter referred to by the cultivar name 'Balobwablu'.

This new cultivar originated in a controlled breeding program during August 2001 at Arroyo Grande, Calif. The objective of the breeding program was the development of new *Lobelia* cultivars with unique flower colors and vigorous, trailing growth habits.

The new cultivar was the result of the open-pollination of *Lobelia erinus* cultivar Wesstar, U.S. Plant Pat. No. 12,678, which requires long days to bloom, exhibits white-colored flowers, and has a heavily branching, mounded, and trailing growth habit. The resulting seed was collected and germinated. From the flowering progeny, a single plant was discovered and selected by the inventor during January 2002.

Asexual reproduction of the new cultivar by terminal or stem cuttings since 2002 at Arroyo Grande, Calif., and West Chicago, Ill. has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

The following characteristics of the new cultivar have been repeatedly found and can be used to distinguish 'Balobwablu' as a new and distinct cultivar of *Lobelia* plant:

1. Mounded and trailing growth habit.
2. Dark lavender blue-colored flowers.
3. Dark green-colored foliage.
4. Day length neutral flowering habit.

Plants of the new cultivar differ from plants of the female parent primarily in flower color and day length requirement.

Of the *Lobelia* cultivars known to the inventor, the most similar to the new cultivar is the *Lobelia* cultivar 'Periwinkle Blue', U.S. Plant Pat. No. 12,536. However in side-by-side comparisons, plants of the new cultivar differ from plants of 'Periwinkle Blue' in the following characteristics:

1. Plants of the new cultivar exhibit a more spreading growth habit than plants of 'Periwinkle Blue'.
2. The flowers of the new cultivar are a different color than the flowers of 'Periwinkle Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describes the colors of 'Balobwablu'. The plants were grown in 10 cm pots for 13 weeks in a greenhouse at West Chicago, Ill.

DETAILED BOTANICAL DESCRIPTION

Figure 1:
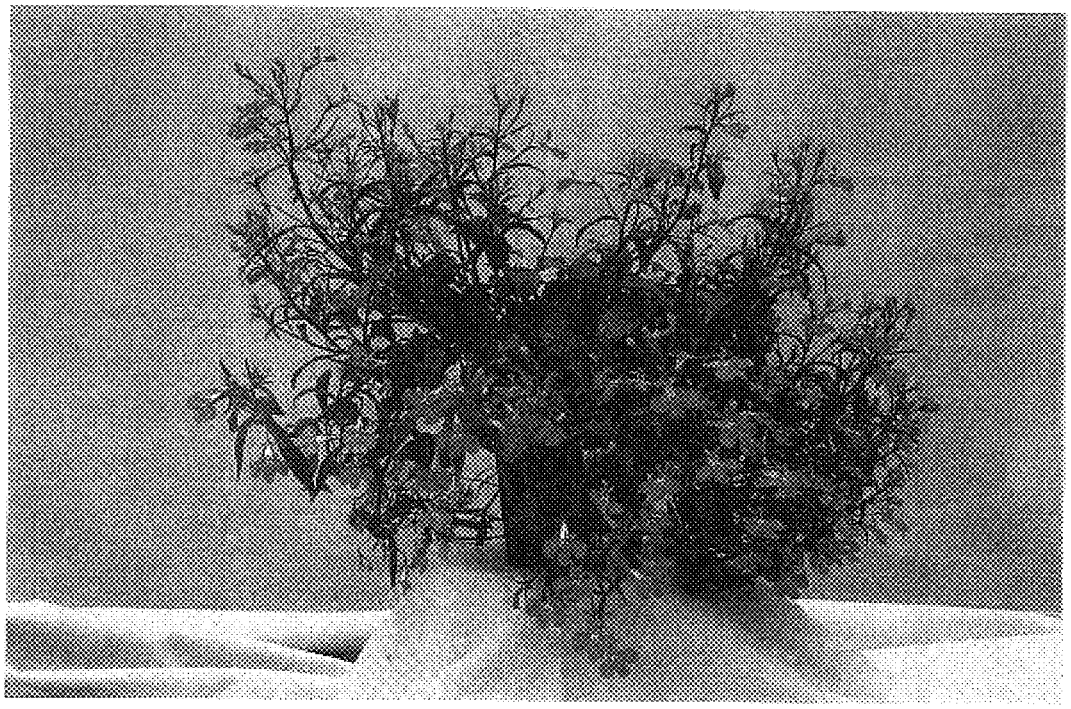
FIG. 1 illustrates a side view of the general growth habit of 'Balobwablu'.
Figure 2:
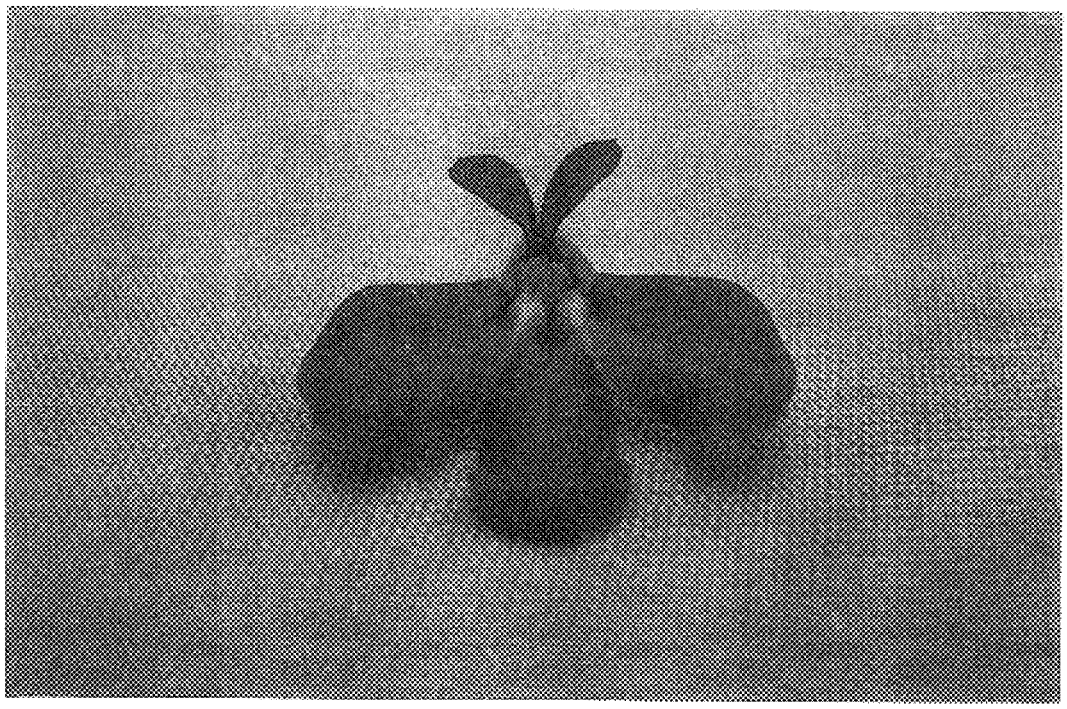
FIG. 2 illustrates a close-up view of an individual flower of 'Balobwablu'.

The chart used in the identification of colors described herein is the R.H.S. Colour Chart of The Royal Horticultural Society, London, England, 2001 edition, except where color terms of ordinary significance are used. The color values were determined on Sep. 27, 2004 in West Chicago, Ill. between 1:00 and 1:45 p.m. under natural light conditions.

The following descriptions and measurements describe plants produced from cuttings taken from stock plants and grown in a double polycarbonate-covered under greenhouse under conditions comparable to those used in commercial practice. Plants were grown in 10 cm pots for 13 weeks while utilizing a soil-less growth medium. Greenhouse temperatures were maintained at approximately 70–75° F. (21–24° C.) during the day and approximately 55–60° F.

(13–14° C.) during the night. Greenhouse light levels were maintained at approximately 5,000–8,000 footcandles during the day.

Botanical classification: *Lobelia erinus* cultivar Balobwablu.

Parentage: Open pollination of 'Wesstar', U.S. Plant Pat. No. 12,678.

Propagation:

*Type cutting.*—Terminal stem.

*Time to initiate roots.*—Approximately 6–9 days.

*Time to produce a rooted cutting.*—Approximately 28 days.

*Root description.*—Fibrous.

*Rooting habit.*—Freely branching.

Plant description:

*Crop time.*—Approximately 9–10 weeks.

*Growth habit.*—Vigorous and freely branching with lateral branches at every node.

*Form.*—Mounded and trailing.

*Size.*—Height from soil level to top of plant plane: Approximately 17.5 cm. Diameter (area of spread): Approximately 43.9 cm.

*Branch description.*—Quantity of main branches: 4. Strength: Strong. Length: Approximately 28.4 cm. Diameter: Approximately 2 mm. Texture: Glabrous. Color: Closest to 137A. Length of internode at middle of branch: Approximately 2.3 cm.

*Foliage.*—Quantity of leaves per main branch: Approximately 12. Fragrance: None. Form: Simple. Arrangement: Alternate. Aspect: At acute angle to the stem. Base: Attenuate, sessile. Texture of upper and lower surface: Glabrous.

*Apical leaves.*—Shape: Lanceolate. Margin: Entire. Apex: Mucronate. Length: Approximately 3.3 cm. Width: Approximately 6.3 mm. Venation pattern: Pinnate. Color of upper surface of mature foliage: Closest to 137A with venation of 144B. Color of lower surface of mature foliage: Closest to 187B overlaid with 143A and venation of 143B.

*Basal leaves.*—Shape: Ovate. Margin: Lobed. Apex: Mucronate. Length: Approximately 2.8 cm. Width: Approximately 2 mm. Color of upper surface of mature foliage: Closest to 144A with venation of 143B. Color of lower surface of mature foliage: 144B with irregular areas of 176C and venation of 143B. Petiole length: Approximately 8.9 mm. Petiole diameter: Approximately 2.8 mm. Petiole texture: Glabrous on both surfaces. Color of upper surface of petiole: 144A. Color of lower surface of petiole: 144B.

Flowering description:

*Flowering habit.*—'Balobwablu' is freely flowering under outdoor growing conditions with substantially continuous blooming from spring until autumn and year round in greenhouse environment.

*Lastingness of bloom.*—Approximately 6–9 days.

*Quantity of flowers per lateral branch.*—Approximately 7.

Flower description:

*Flower bud.*—Rate of opening: Generally takes 3–6 days for buds to progress from first color to fully open flowers. Shape: Oblong. Length: Approximately 1.3 cm. Diameter: Approximately 5 mm. Texture: Glabrous. Color: Tube is 155C, petals are closest to 122B.

*Quantity of flowers.*—One per axil.

*Flower aspect.*—Pointing outwardly, inverted because of twisted pedicel.

*Flower form.*—Ampliate, labiate. Upper lip consists of two narrow petals; lower lip consists of three broader petals. Petals are fused at base forming a tube which is split between the two upper petals.

*Flower size.*—Diameter/width: Approximately 2.1 cm. Length: Approximately 1.9 cm. Depth: Approximately 4.3 mm.

*Corolla tube.*—Split almost to base along one side. Length: Approximately 1 cm. Diameter at base: Approximately 2.2 mm. Diameter at throat: Approximately 4 mm. Texture of inner and outer surface: Glabrous. Color of outer surface: Closest to 95D. Color of inner surface: 95D with one stripe of 86A, one stripe of 86B, and spots of 1B.

*Petals.*—Margin: Entire. Texture: Glabrous at margin and center, pubescent at base.

*Upper petals.*—Shape: Oblanceolate. Length: 6.8 mm. Width at apex: 2.5 mm. Color of upper surface: Darker and redder than 94A. Color of lower surface: 96C. Petals fade with age to: 95C.

*Lower petals.*—Shape: Obovate. Length: 1.1 cm. Width at apex: 7.9 mm. Color of upper surface: Closest to but darker and redder than 94A. Color of lower surface: 96C.

*Pedicel.*—Length: Approximately 2.5 cm. Diameter: Approximately 0.6 mm. Texture: Glabrous. Color: Closest to 137A.

*Sepals.*—Five, fused to form calyx. Shape: Linear. Apex: Narrow acute. Margin: Entire. Texture: Glabrous. Color: 137A.

*Calyx.*—Length: Approximately 6.7 mm. Diameter at base: Approximately 1.5 mm. Diameter at petals: Approximately 1.3 cm.

*Reproductive organs.*—Stamen quantity: 5 fused around pistil. Filament length: Approximately 9 mm. Filament color: 91A. Anther shape: Linear. Anther length: Approximately 2.2 mm. Anther color: N92C. Amount of pollen: Moderate. Pollen color: N155B. Pistil quantity: One. Length: Approximately 1.5 cm. Sigma shape: Round. Stigma diameter: Approximately 1.5 mm. Stigma color: 90C. Style length: 8.5 mm. Style color: N144D. Ovary size: 4.9 mm. Ovary color: Closest to 143A.

Seed and fruit development: Neither seed nor fruit production has been observed.

Disease and pest resistance: Resistance to pathogens and pests common to *Lobelia* has not been observed.

What is claimed is:

1. A new and distinct cultivar of *Lobelia* plant named 'Balobwablu', substantially as herein illustrated and described.

* * * * *